United States Patent
Evancich et al.

(10) Patent No.: US 8,793,254 B2
(45) Date of Patent: Jul. 29, 2014

(54) METHODS AND APPARATUS FOR CLASSIFYING CONTENT

(76) Inventors: Nicholas H. Evancich, Clarksburg, MD (US); Patrick Bohan, Silver Spring, MD (US); Grant Verstandig, Arlington, VA (US)

(*) Notice: Subject to any disclaimer, the term of this patent is extended or adjusted under 35 U.S.C. 154(b) by 0 days.

(21) Appl. No.: 13/587,588

(22) Filed: Aug. 16, 2012

(65) Prior Publication Data

US 2013/0212109 A1 Aug. 15, 2013

Related U.S. Application Data

(60) Provisional application No. 61/524,915, filed on Aug. 18, 2011.

(51) Int. Cl.
*G06F 17/30* (2006.01)
(52) U.S. Cl.
USPC .......................................... 707/740
(58) Field of Classification Search
USPC ................. 707/3, 709, 740; 705/37
See application file for complete search history.

(56) References Cited

U.S. PATENT DOCUMENTS

| | | | |
|---|---|---|---|
| 6,039,688 A | 3/2000 | Douglas et al. | |
| 6,339,410 B1 | 1/2002 | Milner et al. | |
| 6,368,273 B1 | 4/2002 | Brown | |
| 6,454,705 B1 | 9/2002 | Cosentino et al. | |
| 6,849,045 B2 | 2/2005 | Iliff | |
| 7,357,639 B2 | 4/2008 | Stillman | |
| 7,379,867 B2 | 5/2008 | Chelba et al. | |
| 7,603,282 B2 | 10/2009 | Imai et al. | |
| 7,624,006 B2 | 11/2009 | Chelba et al. | |
| 7,672,940 B2 * | 3/2010 | Viola et al. | 707/999.006 |
| 7,765,113 B2 | 7/2010 | Ware et al. | |
| 7,970,767 B2 | 6/2011 | Probst et al. | |
| 2003/0135095 A1 | 7/2003 | Iliff | |
| 2004/0138924 A1 | 7/2004 | Pristine | |
| 2004/0181432 A1 | 9/2004 | Senba et al. | |
| 2006/0253365 A1* | 11/2006 | Langshur et al. | 705/37 |
| 2007/0055612 A1 | 3/2007 | Palestrant et al. | |
| 2007/0219776 A1 | 9/2007 | Gamon et al. | |
| 2009/0048927 A1 | 2/2009 | Gross | |
| 2010/0125564 A1* | 5/2010 | Strohm et al. | 707/709 |
| 2011/0046980 A1 | 2/2011 | Metzler et al. | |
| 2011/0046981 A1 | 2/2011 | Metzler et al. | |

(Continued)

OTHER PUBLICATIONS

Final Office Action for U.S. Appl. No. 13/404,801, mailed Feb. 7, 2013.

(Continued)

*Primary Examiner* — Etienne Leroux
(74) *Attorney, Agent, or Firm* — Cooley LLP

(57) ABSTRACT

In some embodiments, a non-transitory processor-readable medium includes code to cause a processor to send a signal representing a first question and a set of pictogram answers associated with the first question and a second question, different from the first question, and a set of pictogram answers associated with the second question. The first question and the second question can define a health-related survey such as a health-risk assessment. The non-transitory processor-readable medium includes code to receive a user selection of a pictogram answer associated with the first question and receive a user selection of a pictogram answer associated with the second question. The non-transitory processor-readable medium includes code to define a health-related user profile based on the user selection to the first question and the second question.

22 Claims, 5 Drawing Sheets

(56) References Cited

U.S. PATENT DOCUMENTS

| | | |
|---|---|---|
| 2011/0047508 A1 | 2/2011 | Metzler et al. |
| 2011/0099027 A1 | 4/2011 | Weathers |
| 2012/0158616 A1 | 6/2012 | Verstandig et al. |
| 2013/0046552 A1 | 2/2013 | Verstandig et al. |

OTHER PUBLICATIONS

International Search Report and Written Opinion for PCT/US2012/051096, mailed Nov. 2, 2012.
U.S. Appl. No. 13/310,373, filed Dec. 2, 2011.
Office Action for U.S. Appl. No. 13/404,801, mailed Feb. 24, 2012.
International Search Report and Written Opinion for PCT/US2012/051249, mailed Jan. 24, 2013.
Vester et al. "Information Retrieval in Document Spaces Using Clustering," in: [online]. Retrieved on Oct. 11, 2012. Retrieved from the Internet at URL: <http://www2.imm.dtu.dk>, Dated Aug. 2005, 255 pages.
Cardillo "A Lexi-Ontological Resource for Consumer Healthcase." in: [online], Retrieved on Oct. 11, 2012, Retrieved from the Internet at URL: <http://eprints-phd.biblio.unitn.it/570/1/PhD-Thesis-Elena-Cardillo.pdf>, Dated Apr. 2011, 210 pages.

* cited by examiner

400

```
┌─────────────────────────────────────────────────────────────┐
│ Categorize a first natural language document as related to  │
│                  a term based on a training set.            │
│                            402                              │
└─────────────────────────────────────────────────────────────┘
                              ↓
┌─────────────────────────────────────────────────────────────┐
│ Send an indication that the first natural language document │
│                    is related to the term.                  │
│                            404                              │
└─────────────────────────────────────────────────────────────┘
                              ↓
┌─────────────────────────────────────────────────────────────┐
│ Receive at least a portion of each message from a set of    │
│ messages posted by a set of users on a website and          │
│              associated with the term.                      │
│                            406                              │
└─────────────────────────────────────────────────────────────┘
                              ↓
┌─────────────────────────────────────────────────────────────┐
│ Identify a keyword absent from the training set based on    │
│ the set of messages when usage of the keyword within the    │
│            set of messages exceeds a threshold.             │
│                            408                              │
└─────────────────────────────────────────────────────────────┘
                              ↓
┌─────────────────────────────────────────────────────────────┐
│ Modify the training set to include the keyword in response  │
│       to the identifying to define a modified training set. │
│                            410                              │
└─────────────────────────────────────────────────────────────┘
                              ↓
┌─────────────────────────────────────────────────────────────┐
│ Categorize a second natural language document as related    │
│         to the term based on the modified training set.     │
│                            412                              │
└─────────────────────────────────────────────────────────────┘
                              ↓
┌─────────────────────────────────────────────────────────────┐
│ Send an indication that the second natural language         │
│              document is related to the term.               │
│                            414                              │
└─────────────────────────────────────────────────────────────┘
```

```
┌─────────────────────────────────────────────────────────────────────┐
│ Define a training set for a first term based on a set of keywords   │
│ from a first natural language document defining the first term and  │
│ a set of keywords from a second natural language document           │
│ defining the first term.                                            │
│                              502                                    │
└─────────────────────────────────────────────────────────────────────┘
                                  │
                                  ▼
┌─────────────────────────────────────────────────────────────────────┐
│ Define a training set for a second term based on a set of keywords  │
│ from a third natural language document defining the second term     │
│ and a set of keywords from a fourth natural language document       │
│ defining the second term.                                           │
│                              504                                    │
└─────────────────────────────────────────────────────────────────────┘
                                  │
                                  ▼
┌─────────────────────────────────────────────────────────────────────┐
│ Define a training set for a third term based on the training set    │
│ for the first term and the training set for the second term, the    │
│ third term is associated with the first term and the second term.   │
│                              506                                    │
└─────────────────────────────────────────────────────────────────────┘
                                  │
                                  ▼
┌─────────────────────────────────────────────────────────────────────┐
│ Categorize a fifth natural language document as related to the      │
│ third term based on the training set for the third term.            │
│                              508                                    │
└─────────────────────────────────────────────────────────────────────┘
                                  │
                                  ▼
┌─────────────────────────────────────────────────────────────────────┐
│ Send an indication that the fifth natural language document is      │
│ related to the third term.                                          │
│                              510                                    │
└─────────────────────────────────────────────────────────────────────┘
```

FIG. 5

METHODS AND APPARATUS FOR CLASSIFYING CONTENT

CROSS REFERENCE TO RELATED APPLICATION

This application claims priority to and the benefit of U.S. Provisional Patent Application Ser. No. 61/524,915, filed Aug. 18, 2011, entitled "System and Method for Exchanging Healthcare Information," the disclosure of which is hereby incorporated by reference in its entirety.

BACKGROUND

Some embodiments described herein relate generally to classification of natural language documents, and more particularly, apparatus and methods for classifying text content of natural language documents based on training sets.

Some known systems such as recommendation engines implement a standard approach to classify text content of natural language documents based on a training set associated with a term of interest. Such a training set used by these known systems is typically defined based on a specific single resource of the term of interest. Such known systems, however, typically do not provide a method to define the training set based on multiple resources of the term of interest, or automatically update the training set based on new information or resource(s) related to the term of interest. As a result, the training sets used in those known systems can be inaccurate or outdated in some scenarios.

Accordingly, a need exists for systems and methods for classifying text content of natural language documents based on training sets that can be defined based on multiple resources and automatically updated.

SUMMARY

In some embodiments, a non-transitory processor-readable medium includes code to cause a processor to receive at least a portion of a first natural language document defining a term and having a set of keywords, and at least a portion of a second natural language document defining the term and having a set of keywords different from the set of keywords from the first natural language document. The non-transitory processor-readable medium includes code to cause the processor to automatically define a training set based on the set of keywords from the first natural language document and the set of keywords from the second natural language document. The non-transitory processor-readable medium includes code to cause the processor to categorize a third natural language document as related to the term based on the training set, and further send an indication that the third natural language document is related to the term.

BRIEF DESCRIPTION OF THE DRAWINGS

FIG. 4 is a flow chart illustrating a method of modifying a training set used to classify content, according an embodiment.

FIG. 5 is a flow chart illustrating a method of defining training sets used to classify content, according to an embodiment.

DETAILED DESCRIPTION

Figure 1:
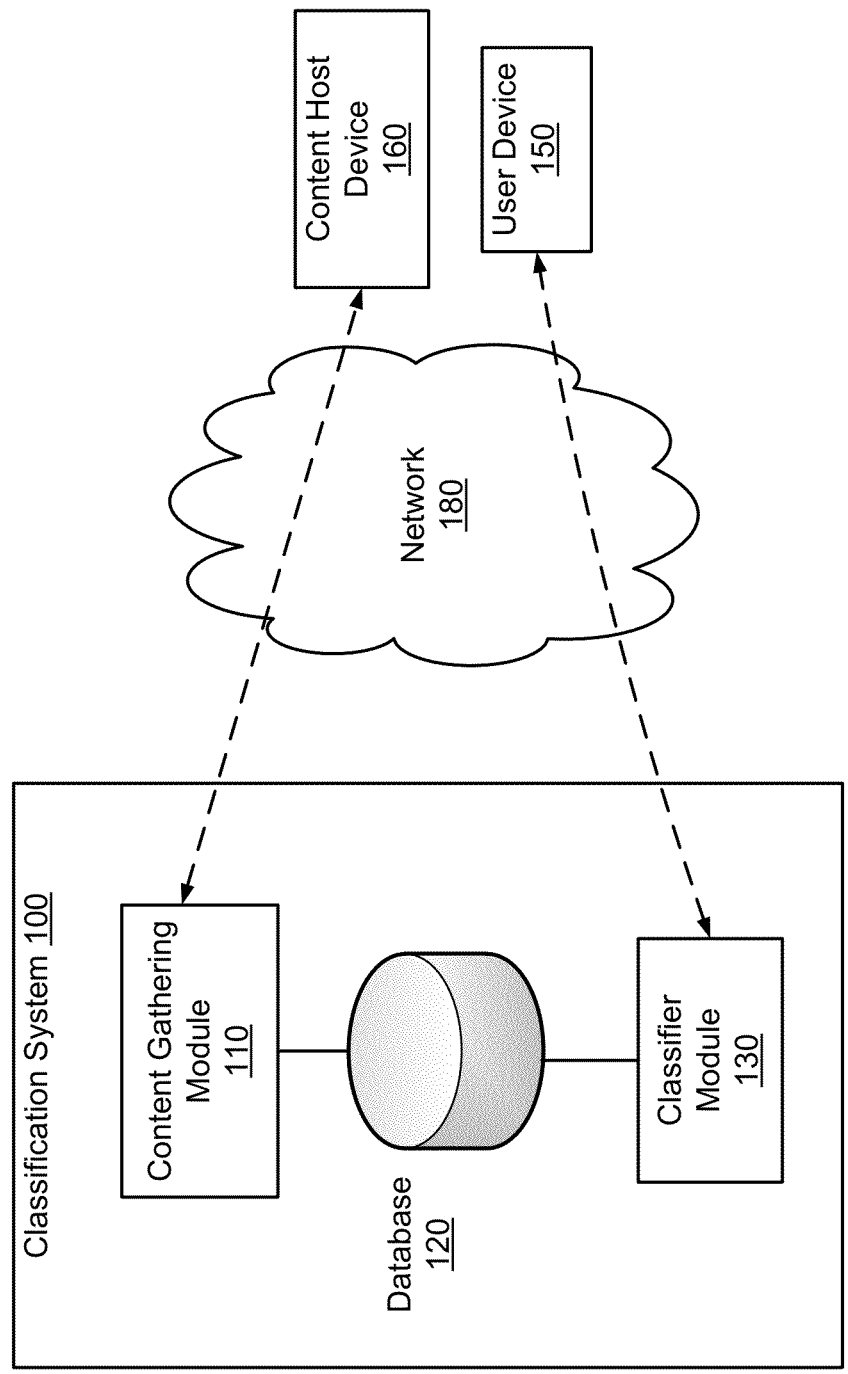
FIG. 1 is a schematic illustration of a classification system configured to classify content, according to an embodiment.

In some embodiments, a non-transitory processor-readable medium stores code representing instructions to be executed by a processor. The non-transitory processor-readable medium includes code to cause a processor to receive at least a portion of a first natural language document defining a term and having a set of keywords, and at least a portion of a second natural language document defining the term and having a set of keywords different from the set of keywords from the first natural language document. In some embodiments, the portion of the first natural language document is received from a crawl engine that searched a website. The portion of the second natural language document is also received from the crawl engine that searched a website different from the website for the first natural language document.

In some embodiments, the term is a medical condition. The first natural language document is associated with a medical website, and the term is defined within the first natural language document using the set of keywords from the first natural language document. The second natural language document is associated with a medical website different from the medical website associated with the first natural language document, and the term is defined within the second natural language document using the set of keywords from the second natural language document.

The non-transitory processor-readable medium includes code to cause the processor to automatically define a training set based on the set of keywords from the first natural language document and the set of keywords from the second natural language document. In some embodiments, the code to define includes code to identify a subset of keywords included in the set of keywords from the first natural language document and included in the set of keywords from the second natural language document, where the training set includes the subset of keywords.

The non-transitory processor-readable medium includes code to cause the processor to categorize a third natural language document as related to the term based on the training set, and further send an indication that the third natural language document is related to the term. In some embodiments, the code to categorize includes code to categorize the third natural language document as related to the term when usage of keywords from the subset of keywords within the third natural language document exceeds a threshold.

In some embodiments, the non-transitory processor-readable medium further includes code to cause the processor to receive at least a portion of each message from a set of messages posted by a set of users on a website and associated with the term. The non-transitory processor-readable medium includes code to cause the processor to identify a keyword absent from the training set based on the set of messages when usage of the keyword within the set of messages exceeds a threshold. The non-transitory processor-readable medium includes code to cause the processor to modify the training set to include the keyword in response to the identifying to define a modified training set. The non-transitory processor-readable medium also includes code to cause the processor to categorize a fourth natural language document as related to the term based on the modified training set, and further send an indication that the fourth natural language document is related to the term.

In some embodiments, the term is a first term, and the training set is for the first term. The non-transitory processor-readable medium further includes code to cause the processor to define a training set for a second term based on a set of keywords from a third natural language document defining the second term and a set of keywords from a fourth natural language document defining the second term. The non-transitory processor-readable medium includes code to cause the processor to define a training set for a third term based on the training set for the first term and the training set for the second term, where the third term includes the first term and the second term. The non-transitory processor-readable medium includes code to cause the processor to categorize a fifth natural language document as related to the third term based on the training set for the third term, and further send an indication that the fifth natural language document is related to the third term.

As used in this specification, the singular forms "a," "an" and "the" include plural referents unless the context clearly dictates otherwise. Thus, for example, the term "network" is intended to mean a single network or a combination of networks.

FIG. 1 is a schematic illustration of a classification system 100 configured to classify content, according to an embodiment. The classification system 100 can be hosted at one or more devices that are operatively coupled to each other. The device(s) hosting the classification system 100 can be operatively coupled to and communicate with (e.g., send data to and/or receive data from) one or more content host devices (e.g., the content host device 160) and/or one or more user devices (e.g., the user device 150). In some embodiments, a device hosting the classification system 100 or a portion of the classification system 100 can be configured to function as, for example, a server device, a network management device, a data storage device, and/or so forth.

As shown in FIG. 1, the classification system 100 includes a content gathering module 110, a database 120 and a classifier module 130. In some embodiments, the classification system 100 can include more modules and/or components than those shown in FIG. 1. The modules or components included in the classification system 100 can be, for example, hardware modules, software modules (stored and/or executing in hardware) stored in one or more memories (not shown in FIG. 1) associated with the classification system 100 and executed by one or more processors (not shown in FIG. 1) of the classification system 100, and/or any combination of hardware modules and software modules.

In some embodiments, the modules and components included in the classification system 100 can be configured to perform various aspects and/or operations to classify content. Specifically, the content gathering module 110 can be configured to gather content from, for example, one or more content host devices (e.g., the content host device 160) operatively coupled to the classification system 100. The database 120 can be any data structure used to store content gathered by the content gathering module 110. The classifier module 130 can be configured to classify content stored in the database 120 based on, for example, one or more training sets. In some embodiments, the classifier module 130 can be configured to modify or update the training sets such that accuracy of the classifying operations can be improved.

Figure 2:
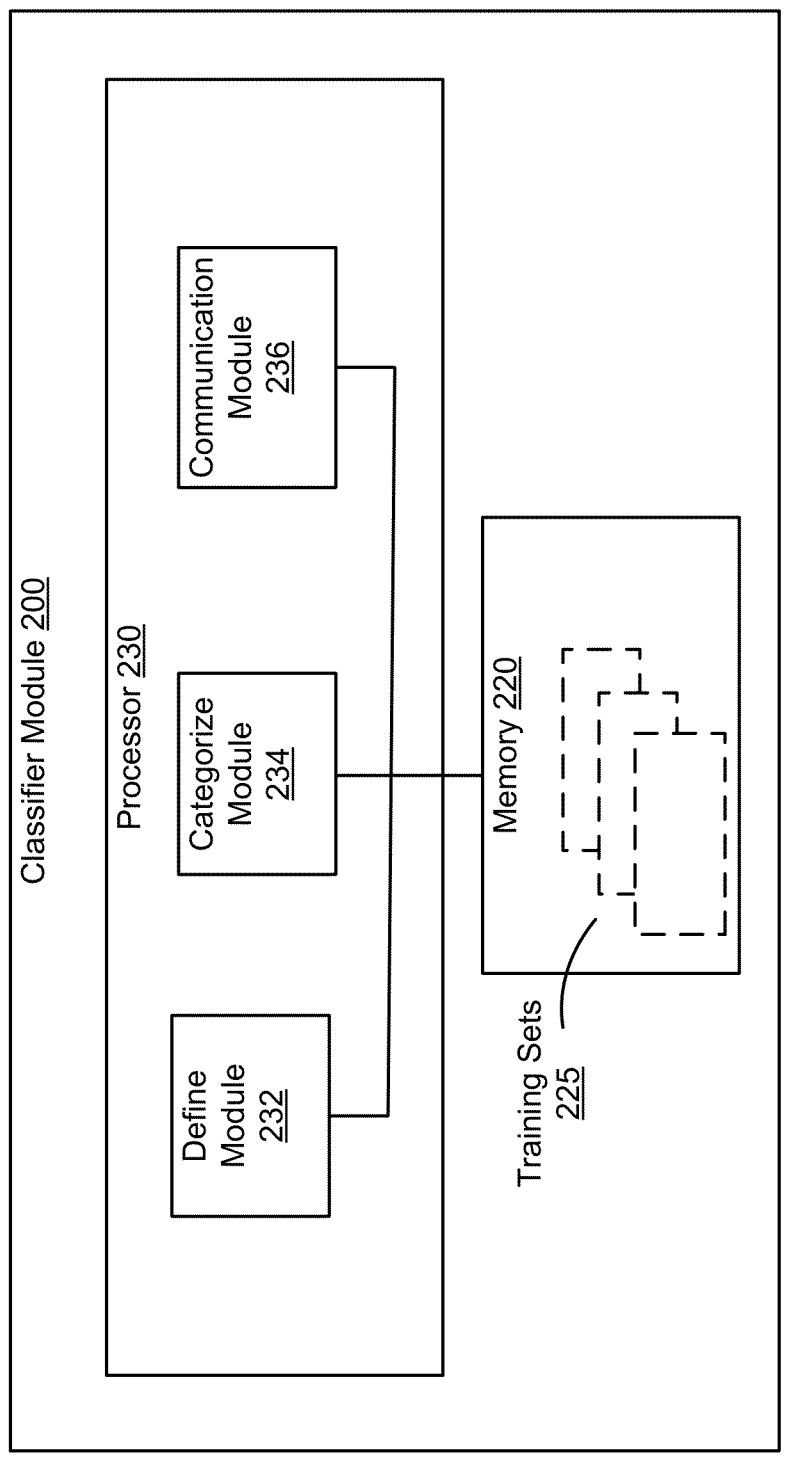
FIG. 2 is a block diagram of a classifier module, according to an embodiment.

FIG. 2 is a block diagram of a classifier module 200, according to an embodiment. The classifier module 200 can be structurally and functionally similar to the classifier module 130 shown in FIG. 1. Particularly, the classifier module 200 can be included in a classification system similar to the classification system 100 in FIG. 1, and operatively coupled to a content gathering module and a database that are similar to the content gathering module 110 and the database 120 in FIG. 1, respectively.

As shown in FIG. 2, the classifier module 200 includes a memory 220 and a processor 230. Although FIG. 2 shows the memory 220 and the processor 230 being part of the classifier module 200, it should be understood that the memory 220 and the processor 230 can also implement other modules or components of the classification system that includes the classifier module 200, such as the content gathering module and the database included in the classification system.

The processor 230 can be any suitable processor such as, for example, a general purpose processor, a central processing unit (CPU), a network processor, a front end processor, an accelerated processing unit (APU), and/or the like. As such, the processor 230 can be configured to run and/or execute a set of instructions stored in, for example, the memory 220. The processor 230 includes a define module 232, a categorize module 234 and a communication module 236, which are collectively configured to execute a classification method to classify content. In some embodiments, the processor 230 can include more or less modules associated with executing the classification method than those shown in FIG. 2. For example, the communication module 236 can be optional, and the remaining modules and/or potions of the classifier module 200 can be configured to communicate with each other and with external devices or modules without assistance of a communication module. Each of the modules included in the processor 230 can be, for example, a hardware module, a software module (stored and/or executing in hardware) or a combination of a hardware module and a software module, where the processor 230 is configured to execute at least a portion of the classification method.

The memory 220 can be any storage device such as, for example, a random access memory (RAM), a memory buffer, a hard drive, and/or so forth. In some embodiments, the memory 220 can store instructions to cause the processor 230 to execute modules (e.g., the define module 232, the categorize module 234, the communication module 236), processes, and/or functions associated with the classification method. In some embodiments, the memory 220 can include one or more training sets 225. The training sets 225 can be used during execution of the classification method, as described in detail below.

Returning to FIG. 1, the classification system 100 is operatively coupled to the content host device 160 and the user device 150 via, for example, the network 180. In some embodiments, the classification system 100 can be operatively coupled to any number of content host devices and/or any number of user devices. In some embodiments, as shown in FIG. 1, the content host device 160 is operatively coupled to the content gathering module 110 of the classification system 100, and the user device 150 is operatively coupled to the classifier module 130 of the classification system 100. In other embodiments, the content host device 160 and the user device 150 can be operatively coupled to other modules and/or or components of the classification system 100.

The content host device 160 can be any device that makes content available for other devices to read or retrieve. Similarly stated, the content host device 160 can be configured to host, store and/or maintain content. The content available at the content host device 160 can be, for example, text content (e.g., an article), image content (e.g., an image file), video content (e.g., a video clip), audio content (e.g., an audio message), and/or any other type of content. In some embodiments, the content host device 160 can host a mix of content in various formats (e.g., text, audio, image, and/or video). In some embodiments, the content host device 160 can be, for example, a web server, a network server, a network management device, and/or the like. For example, the content host device 160 can be a web server hosting a medical website that includes articles, posts, discussion threads, and/or messages associated with medical conditions. For another example, the content host device 160 can be a social media platform such as Facebook, Twitter, Google+, and/or the like. In some embodiments, the content host device can be a combination (e.g., a network) of multiple server devices.

Although shown in FIG. 1 as the content host device 160 being operatively coupled to the classification system 100 via the network 180, in some other embodiments, the content host device 160 can be directly coupled to or included as a portion of the classification system 100. For example, the content host device 160 can be a storage device (e.g., a memory) included within the device (e.g., a server) hosting the classification system 100. In some embodiments, for example, the classification system 100 can be directly coupled to a local content host device and operatively coupled to a remote content host device via a network.

The user device 150 can be any device that can be used by a user or any other personnel to communicate with the classification system 100. The user device 150 can be, for example, a personal computer, a personal digital assistant (PDA), a smart phone, a video game console, and/or the like. In some embodiments, the user device 150 can be any suitable electronic device configured to send data (e.g., messages) to and/or receive data (e.g., content) from the classification system 100. For example, a user can, using the user device 150, communicate with the classification system 100 over a cellular network (e.g., the network 180) via short message service (SMS), pop-ups, push notification, and/or the like. In some embodiments, the user device 150 can be referred to as a client device and can include a processor, a memory, and a display.

The network 180 can be any type of network that can operatively couple the classification system 100 to other devices including the content host device 160 and the user device 150. In some embodiments, the network 180 can be, for example, a local area network (LAN), a wide area network (WAN), a virtual network, a telecommunications network, a cellular network, the Internet, and/or the like. The network 180 can be implemented as a wired network and/or a wireless network.

In some embodiments, the network 180 can be a network of a single type or a combination of multiple networks of different types. As such, in some embodiments, the classification system 100 can send data to and/or receive data from the content host device 160 and/or the user device 150 using multiple communication modes (e.g., via a website, email, instant messages, barcode transmissions, using a mobile device application, using a personal computer (PC) application, SMS, etc.) associated with the multiple networks included in the network 180. For example, the user device 150 can be a mobile telephone connected to the classification system 100 via a cellular network and the Internet (e.g., the network 180). For another example, the user device 150 can be a personal computer connected to the classification system 100 via an Internet Service Provider (ISP) and the Internet (e.g., the network 180).

The classification system 100 can be configured to classify content. The content gathering module 110 can be configured to gather content. Specifically, the content gathering module 110 can be configured to access, receive, and/or retrieve content from any suitable resource such as, for example, the content host device 160 (via the network 180). In some embodiments, the content gathering module 110 can access and/or receive content from other networks independent of the network 180. For example, the content gathering module 110 can be configured to gather content (e.g., generic natural language documents) from web pages, servers, RSS (rich site summary, or really simple syndication, or RDF (resource description framework) site summary) feeds, chat rooms, blogs, web applications, Twitter accounts, Facebook profiles, other social network accounts or profiles, and/or the like, which are hosted at a content host device or any other device accessible by the classification system 100.

The content gathered by the content gathering module 110 can be any type of media or information (e.g., text, image, audio, video, etc.). The gathered content can be relevant to a user (e.g., to interests of the user) or a term of interest. For example, the content can include informational material, advertising material, health information, activity information, and/or any other content relevant to a user or a term of interest. Particularly, the content gathered by the content gathering module 110 can include content in natural language(s) from natural language documents. A natural language can include, for example, a human language, such as English or Standard Mandarin, as opposed to, for example, constructed language (e.g., Solresol), artificial language (e.g., Lincos), machine language, language of formal logic, or the like. A natural language document can be, for example, an article about a technology posted on a personal blog, a thread of posts related to a product posted on an online forum, a paper on scientific experiments published at a website, and/or the like. The content gathering module 110 can be configured to retrieve at least a portion of such natural language documents in, for example, a text format.

The content gathering module 110 can be configured, for example, to retrieve content from natural language documents based on meta-tags (e.g., keywords) associated with a term of interest. In some embodiments, the content gathering module 110 can be configured to search online and retrieve content from natural language documents related to a certain subject matter or within a certain area associated with the term of interest. In some instances, the term of interest can be, for example, a medical condition. In some instances, the content gathering module 110 can be configured to retrieve content from natural language documents from a certain website based on any suitable criterion without using a term of interest. For example, the content gathering module 110 can be configured to retrieve every paper published during a specific time period from a scientific website. For another example, the content gathering module 110 can be configured to retrieve each article written by a particular author from a personal blog. For yet another example, the content gathering module 110 can be configured to retrieve each discussion thread posted in a particular section of an online forum.

In some embodiments, the content gathering module 110 can be configured to gather content using, for example, a crawl engine. The crawl engine can be an application hosted and executed at a processor of the classification system 100. Such a crawl engine can be configured to search text content at various websites across multiple content host devices (e.g., the content host device 160). In such embodiments, the content gathering module 110 can be configured to operate the crawl engine to search across natural language documents at one or more predetermined websites (e.g., scientific websites, discussion forums, personal blogs, company homepages, etc.) based on one or more keywords associated with a term of interest or any other suitable criterion. After suitable content (e.g., content related to the term of interest, content satisfying the criterion) is found or identified by the crawl engine in the natural language documents from those predetermined websites, the content gathering module 110 can be configured to operate the crawl engine to retrieve the content. The content can be a complete version of a natural language document (e.g., an article) or a portion of the natural language document (e.g., a paragraph in an article).

In some embodiments, additional information associated with the content can also be retrieved (e.g., by the crawl engine) and sent to the content gathering module 110 along with the content. Such additional information can include, for example, a source, length, date of creation and author of the content, and/or the like. The additional information associated with a natural language document can be used in subsequent processing (e.g., classifying, augmenting) of the natural language document. For example, the date of creation of a natural language document can be used in classifying the natural language documents such that that natural language document is grouped with other documents created in the same era. For another example, the author of a natural language document can be used in combining that natural language document with other documents authored by the same author to create a comprehensive document for that author.

For example, the content gathering module 110 can be configured to search (e.g., using a crawl engine) content related to a term "ankylosing spondylitis" across natural language documents from a set of medical websites (e.g., mayoclinic.com, webmd.com). As a result, each piece of content (e.g., a paragraph of an article, an item in a list) containing the term "ankylosing spondylitis" in the set of medical websites can be found or identified (e.g., by the crawl engine) and sent to the content gathering module 110. Additionally, information of the source and date of creation of each piece of content can also be retrieved (e.g., by the crawl engine) and sent to the content gathering module 110 along with that piece of content.

For another example, the content gathering module 110 can be configured to search (e.g., using a crawl engine) content posted on a medical website during the past three years. As a result, each piece of content (e.g., an article, a post, a message) posted on that medical website during the past three years can be found or identified (e.g., by the crawl engine) and sent to the content gathering module 110. Additionally, information of the author, the length, and the date of creation for each piece of content can also be retrieved (e.g., by the crawl engine) and sent back to the content gathering module 110 along with that piece of content.

In some embodiments, the content gathering module 110 can be configured to gather content from resources other than the various websites described herein. The resources can be any type of digital file that contains a natural language document or a portion of a natural language document and can be electronically stored in and/or accessed by a computing device (e.g., a computer, a tablet, a smart phone, etc.). Such a digital file can be located (e.g., stored) remotely or locally to the classification system 100. In such embodiments, the content gathering module 110 can be configured to gather content from the resources using any suitable hardware and/or software (stored in and/or executed by hardware) tools. For example, the content gathering module 110 can be configured to download, using a suitable software tool or application, a digital copy of a journal from a server that is located remotely to the classification system 100. For another example, the content gathering module 110 can be configured to retrieve a list of keywords from a digital image containing text content, which is stored locally in the same device (e.g., a computer) hosting the classification system 100.

After the content is found and received at the content gathering module 110, the content gathering module 110 can be configured to store the content in the database 120. The database 120 can be any suitable database configured to store content (e.g., in the text format or any other suitable format) such as, for example, a relational database, a non-relational database with one or more relational table structures, and/or the like.

In some embodiments, the text content retrieved by the content gathering module 110 can be stored in the form of natural language document(s) in the database 120. The text content included in those natural language documents stored in the database 120 can then be further classified, as described below. In some embodiments, text content retrieved from a single resource (e.g., an article from a blog, a medical website) and/or the same type of resources (e.g., multiple articles from a blog, multiple medical websites) is stored in a single natural language document in the database 120. In some other embodiments, text content retrieved from multiple resources and/or different types of resources (e.g., an article from a blog and a post published on a medical website, a file hosted on a remote server and a document stored at a local hard drive) can be combined and processed (e.g., filtered) to be included in a new natural language document that is stored in the database 120.

In some embodiments, a piece of content stored in the database 120 can be marked as "classified" (or any other indication that the content has been classified) based on, for example, a term of interest associated with that piece of content. In such embodiments, each piece of content associated with a term of interest can be stored at a location within the database 120 that is associated with (e.g., indexed by) the term of interest. Thus, each piece of content associated with a term of interest can be located and retrieved from the database 120 based on the associated term of interest. For example, an article retrieved by the content gathering module 110 based on the term "ankylosing spondylitis" is stored at a location indexed by the term "ankylosing spondylitis" in the database 120. Such an article is marked as "classified" in the database 120, and can be located using the term "ankylosing spondylitis." Furthermore, additional information associated with each piece of content (e.g., source) can be stored along with that piece of content in the database 120.

In some embodiments, a piece of content gathered by the content gathering module 110 that is not based on (e.g., without using) a term of interest can be stored in the database 120 and marked as "unclassified" (or "needs classification," or any other indication that the content has not been classified). In such embodiments, the unclassified content can be stored in any appropriate manner (e.g., at any arbitrary location) in the database 120. For example, the natural language documents posted on the medical website during the past three years are gathered by the content gathering module 110, stored in the database 120 and marked as "unclassified." Furthermore, additional information associated with the unclassified content (e.g., date of creation) can also be stored along with the unclassified content in the database 120.

The classifier module 130 can be configured to classify the content that is stored in the database 120 and marked as "unclassified." In some embodiments, the classifier module 130 can be configured to classify the unclassified content based on one or more training sets stored at the classifier module 130. In some embodiments, for example, a define module within the classifier module 130 is configured to define training sets for the classifier module 130. That is, the define module within the classifier module 130 is configured to generate or form training sets that are used at the classifier module 130 to classify content. The define module of the classifier module 130 can be similar to the define module 232 of the classifier module 200 shown in FIG. 2.

In some embodiments, each training set can be associated with, for example, a term of interest (e.g., a subject matter, a keyword). The define module of the classifier module 130 can be configured to define such a training set for the term of interest based on content associated with the term of interest that is stored and classified in the database 120. In some embodiments, the define module of the classifier module 130 can be configured to automatically define a training set for the classification system 100 upon relevant content being stored and classified in the database 120. That is, the define module of the classifier module 130 can be configured to execute instructions and/or codes associated with defining the training set within a predetermined time period after the relevant content is stored and classified in the database 120, without being triggered by any external instruction or command (e.g., from an operator of the classification system 100). In some other embodiments, the define module of the classifier module 130 can be configured to define a training set based on, for example, an instruction or command from an operator of the classification system 100.

In some embodiments, the define module of the classifier module 130 can be configured to retrieve a piece of content (e.g., a portion of a natural language document) from the database 120, which defines and classifies the term of interest. That is, the piece of content retrieved by the classifier module 130 includes content associated with a definition for the term of interest. The define module of the classifier module 130 can be configured to determine a set of keywords associated with defining the term of interest from the piece of content. The define module of the classifier module 130 can be configured to define the training set for the term of interest based on the determined set of keywords. For example, such a training set can include or correspond to the set of keywords. For another example, such a training set can include or correspond to a subset of the set of keywords (e.g., depending on the frequency of each keyword occurring in the piece of content).

In some embodiments, when more than one piece of content (e.g., multiple natural language documents) is stored and classified in the database 120, and defines the term of interest, the define module of the classifier module 130 can be configured to define the training set for the term of interest based on the more than one piece of content. Specifically, the define module of the classifier module 130 can be configured to retrieve each piece of content defining the term of interest, and determine a set of keywords associated with defining the term of interest from each retrieved piece of content. The define module of the classifier module 130 can be configured to define the training set for the term of interest based on the multiple determined sets of keywords. Such a training set can be defined in any suitable way. For example, such a training set can be formed by a union of the multiple sets of keywords (including each keyword from the multiple sets of keywords). For another example, such a training set can be formed by an intersection of the multiple sets of keywords (including each keyword that occurs in each set of keywords from the multiple sets of keywords). For yet another example, such a training set can be formed by a subset of each set of keywords from the multiple sets of keywords (including each keyword that occurs at least a predetermined number of times in each set of keywords from the multiple sets of keywords).

In some embodiments, the define module of the classifier module 130 can be configured to determine keywords associated with defining the term of interest from the content defining the term of interest using, for example, a suitable predetermined process, method, set of instructions, program, and/or the like. The define module of the classifier module 130 can be configured to define the training set based on one or more sets of keywords using, for example, a suitable predetermined process, method, set of instructions, program, and/or the like.

Consider an example where the define module of the classifier module 130 retrieves two pieces of content defining the term "ankylosing spondylitis" from the database 120. The first piece of content is gathered by the content gathering module 110 (e.g., using a crawl engine) from an article posted on mayoclinic.com, and is as follows:

"Ankylosing spondylitis: Ankylosing spondylitis is an inflammatory disease that can cause some of the vertebrae in your spine to fuse together. This fusing makes the spine less flexible and can result in a hunched-forward posture. A severe case of ankylosing spondylitis can make it impossible for you to lift your head high enough to see forward. Ankylosing spondylitis affects men more often than women. Signs and symptoms of ankylosing spondylitis typically begin in early adulthood. Inflammation also can occur in other parts of your body—such as your eyes and bowels. There is no cure for ankylosing spondylitis, but treatments can decrease your pain and lessen your symptoms."

The second piece of content is gathered by the content gathering module 110 (e.g., using the crawl engine) from another article posted on webmd.com, and is as follows:

"Ankylosing spondylitis: Ankylosing spondylitis is a type of arthritis that affects the spine Ankylosing spondylitis symptoms include pain and stiffness from the neck down to the lower back. The spine's bones (vertebrae) may grow or fuse together, resulting in a rigid spine. These changes may be mild or severe, and may lead to a stooped-over posture. Early diagnosis and treatment helps control pain and stiffness and may reduce or prevent significant deformity."

Using a predetermined method (e.g., compare content with a predetermined set of medical keywords and identify each medical keyword that occurs in the content), the define module of the classifier module 130 is configured to determine a first set of keywords from the first piece of content, which includes: ankylosing, spondylitis, inflammation, disease, spine, fuse, posture, pain, vertebrae, affects, eyes, bowels, treatments, adulthood, and symptom. Similarly, using the same predetermined method, the define module of the classifier module 130 is configured to determine a second set of keywords from the second piece of content, which includes: ankylosing, spondylitis, arthritis, spine, fuse, posture, pain, stiffness, neck, bones, vertebrae, affects, stiffness, deformity, and symptom.

The define module of the classifier module 130 is then configured to define a training set for the term "ankylosing spondylitis" based on the two sets of keywords. For example, the training set can be defined as an intersection of the two sets of keywords, which includes: ankylosing, spondylitis, spine, fuse, posture, pain, vertebrae, affects, and symptom. Alternatively, the training set can be defined using any other suitable methods. For example, the training set can be defined as a subset of nouns from the intersection of the two sets of keywords (i.e., spondylitis, spine, fuse, posture, vertebrae, and symptom).

In some embodiments, the define module of the classifier module 130 can be configured to define a training set for a term of interest based on one or more sets of keywords and some additional information associated with the keywords. Such additional information can include, for example, a frequency of each keyword occurring in the corresponding natural language document that is retrieved from the database 120, a word type of each keyword (e.g., noun, adjective, verb), a category of a keyword (e.g., a medical term), etc. For example, a keyword is included in the training set if and only if its occurring frequency is higher than a predetermined threshold. For another example, a keyword in the same category as the term of interest is more likely to be included in the training set than another keyword that is not in the same category as the term of interest.

In some embodiments, the define module of the classifier module 130 can be configured to define a training set for a combined term, which includes multiple individual terms, based on the training sets defined for the multiple individual terms. In some embodiments, the training set for the combined term can be defined as a union, an intersection, or a subset of the intersection of the training sets for the multiple individual terms. In other embodiments, the training set for the combined term can be defined using any other suitable methods based on the training sets for the multiple individual terms. For example, the training set for the term "ankylosing spondylitis" can be defined (e.g., as a union, as an intersection, etc.) based on a training set for the term "ankylosing" and a training set for the term "spondylitis."

After a training set for a term of interest is defined at the define module of the classifier module 130, the define module of the classifier module 130 can be configured to store the training set in a memory of the classifier module 130. Similarly, in FIG. 2, the training sets 225 defined by the define module 232 can be stored in the memory 220 of the classifier module 220 shown in FIG. 2.

In some embodiments, for example, a categorize module of the classifier module 130 can be configured to categorize content that is stored in the database 120 and marked as "unclassified" based on one or more training sets stored at the classifier module 130. The categorize module of the classifier module 130 can be similar to the categorize module 234 of the classifier module 200 shown in FIG. 2. Initially, the categorize module of the classifier module 130 can be configured to filter through the content stored in the database 120, such that the categorize module can identify and retrieve each piece of content marked as "unclassified."

After a piece of unclassified content is retrieved from the database 120, the categorize module of the classifier module 130 can be configured to compare the piece of content with a training set for a term of interest that is available at the classifier module 130. Specifically, the categorize module of the classifier module 130 can be configured to compare the piece of content with the keywords included in the training set (or a subset of the training set). The categorize module of the classifier module 130 can be configured to determine a relevance measure between the piece of content and the training set based on a result of the comparison. For example, such a relevance measure can be determined based on the intersection between the words or terms included in the piece of content and the keywords of the training set (or the subset of the training set): the more keywords are included in the intersection, the higher the relevance measure is. Similarly stated, the more keywords from the training set (or the subset of the training set) are included in the piece of content, the more relevant the piece of content is to the term of interest associated with the training set. In some embodiments, such a relevance measure can be determined for the piece of content based on the training set using any suitable method or measure, such as a Jaccard similarity coefficient, a (mutated) cosine similarity measure, a customized weighted similarity measure, etc.

After a relevancy measure is determined, the categorize module of the classifier module 130 can be configured to determine a categorization result for the piece of content with respect to the term of interest associated with the training set. In some embodiments, the categorize module of the classifier module 130 can determine that (1) the piece of content is related to the term of interest if usage of keywords from the training set (or the subset of the training set) exceeds a threshold, and (2) the piece of content is not related to the term of interest otherwise (that is, the usage of keywords from the training set (or the subset of the training set) does not exceed the threshold). Specifically, the categorize module of the classifier module 130 can be configured to determine that the piece of content is related to the term of interest if the corresponding relevance measure exceeds a predetermined threshold. As a result, the piece of content is marked as "classified" in the database 120. Otherwise, if the corresponding relevance measure does not exceed the predetermined threshold, the categorize module of the classifier module 130 can be configured to determine that the piece of content is not related to the term of interest. As a result, the piece of content remains being marked as "unclassified" in the database 120. The threshold can be determined in any suitable method. For example, the threshold can be determined based on empirical experiments conducted on a set of testing documents. Furthermore, in some embodiments, the threshold can be dynamically adjusted based on the content (e.g., natural language documents) retrieved from the database 120 in real time.

In some embodiments, in addition to associating the piece of content with the term of interest, the categorize module of the classifier module 130 can be configured to classify the piece of content into a particular category with the associated relevancy measure. The particular category can be associated with the term of interest of the training set. Furthermore, in some embodiments, if a piece of content is determined to be related to the term of interest, the classifier module 130 can be configured to send an indication that the piece of content is related to the term of interest. In some embodiments, such an indication can be sent to other components of the classification system 100 or other modules operatively coupled to the classification system 100, such that a recommendation for the piece of content can be provided to users (e.g., via a user device) that are interested in the term. In some other embodiments, such an indication can be directly sent to the users that are interested in the term. In some embodiments, the classifier module 130 can receive an indication of interest for the term from a user (e.g., via a user device operated by the user). In such embodiments, the classifier module 130 can be configured to send the indication that the piece of content is related to the term of interest in response to the indication of interest for the term from the user.

For example, the categorize module of the classifier module 130 can compare a publication on a medical topic with the training set for the term "ankylosing spondylitis," which includes 9 keywords: ankylosing, spondylitis, spine, fuse, posture, pain, vertebrae, affects, and symptom. As a result of the comparison, the intersection between the publication and the training set for "ankylosing spondylitis" includes 5 keywords: ankylosing, spondylitis, posture, pain, and symptom. The categorize module of the classifier module 130 can determine a relevancy measure (e.g., 5/9) between the publication and the training set for "ankylosing spondylitis" based on the intersection. If such a relevancy measure exceeds a predetermined threshold (e.g., 0.5), the categorize module of the classifier module 130 determines that the publication is related to the term "ankylosing spondylitis" with the associated relevancy measure (e.g., 5/9). As a result, the categorize module of the classifier module 130 can classify the publication into a particular category (e.g., a category of "spondylitis") with the associated relevancy measure (e.g., 5/9). The publication can be marked as "classified" in the database 120. Additionally, the classifier module 130 can send an indication that the publication is related to the term "ankylosing spondylitis" in response to an indication of interest for the term "ankylosing spondylitis" from a user, such that a recommendation message related to the publication can be provided to the user. Otherwise, if the relevance measure does not exceed a predetermined threshold (e.g., 0.6), the categorize module of the classifier module 130 determines that the publication is not related to the term "ankylosing spondylitis." As a result, the publication is not classified into the particular category, and it remains being marked as "unclassified" in the database 120.

In some embodiments, the categorize module of the classifier module 130 can be configured to determine a relevance measure between a piece of content and a training set using any suitable method. For example, various priority weights can be given to different keywords in a training set. Following the above example for "ankylosing spondylitis," the keywords "ankylosing" and "spondylitis" can have higher priority weights than the keywords "pain," "affects" and "posture" in the training set for the term "ankylosing spondylitis." As a result, a piece of content including the keyword "ankylosing" or "spondylitis" can have a higher relevancy measure than a piece of content including the keyword "pain," "affects" or "posture" (assuming other conditions are the same for the two pieces of content). In some embodiments, the relevance measure can be determined based on the frequency of a keyword occurring in the piece of content. For example, a piece of content in which the keyword "spondylitis" occurs 6 times can have a higher relevancy measure than another piece of content in which the keyword "spondylitis" occurs 2 times (assuming other conditions are the same for the two pieces of content).

In some embodiments, the categorize module of the classifier module 130 can be configured to compare a piece of content with more than one training set available at the classifier module 130. In such embodiments, similar to the approach described above, the categorize module of the classifier module 130 can be configured to determine a relevancy measure for the piece of content with respect to each of the training sets. As a result, the piece of content can be determined to be related to (or not related to) more than one term of interest, and/or classified (or not classified) into more than one category associated with the corresponding term of interest.

For example, the categorize module of the classifier module 130 can be configured to compare a publication on a medical topic with a first training set for the term "ankylosing spondylitis" and a second training set for the term "tendinitis." The categorize module of the classifier module 130 can determine a relevancy measure for the publication with respect to each of the two training sets. As a result, the publication can be determined to be related to both of the terms, and classified into both of a category of "spondylitis" and a category of "tendinitis" with the associated relevancy measures.

In some embodiments, after a set of pieces of content is determined to be related to a term of interest and classified into a category corresponding to the term of interest, the classifier module 130 can be configured to examine the training set for the term based on the set of pieces of content, and modify the training set accordingly if appropriate. Specifically, the define module of the classifier module 130 can be configured to identify one or more keywords absent from the training set when the usage of the keyword(s) in the set of pieces of content exceeds a threshold. Similarly stated, the define module of the classifier module 130 can be configured to identify each keyword that occurs at least a predetermined number of times in the set of pieces of content but is not included in the training set. As a result, the define module of the classifier module 130 can be configured modify the training set for the term of interest, such that the modified training set includes the keyword(s). Furthermore, the categorize module of the classifier module 130 can be configured to categorize content using the modified training set for the term of interest in the same approach as for using the unmodified training set, as described above.

For example, after 10 messages posted on an online forum are determined to be related to the term "ankylosing spondylitis," the define module of the classifier module 130 can examine the training set for the term "ankylosing spondylitis" based on the 10 messages. As a result of the examination, the define module of the classifier module 130 identifies 4 keywords, stiffness, back, sacroillac and joints, each of which occurs at least 6 times (i.e., a threshold) in the 10 messages and is not included in the training set for the term "ankylosing spondylitis." Thus, the define module of the classifier module 130 can modify the training set for the term "ankylosing spondylitis," such that the modified training set for the term "ankylosing spondylitis" includes the 4 keywords. Consequently, the modified training set for the term "ankylosing spondylitis" includes: ankylosing, spondylitis, spine, fuse, posture, pain, vertebrae, affects, symptom, stiffness, back, sacroillac and joints. Furthermore, the categorize module of the classifier module 130 can categorize content using the modified training set for the term "ankylosing spondylitis," accordingly.

In some embodiments, a content extracting module (not shown in FIG. 1 or FIG. 2) can be included in the classification system 100. The content extracting module can be used to filter through the content stored in the database 120 and retrieve the pieces of content marked as "unclassified." Furthermore, the content extracting module can be configured to extract, from the retrieved content, a portion of content (e.g., keywords) associated with the classification, and then send the extracted content to the categorize module of the classifier module 130. After the extracted content is received at the categorize module of the classifier module 130, the categorize module of the classifier module 130 can be configured to categorize the unclassified content by comparing the extracted content to the training set(s), similar to the approach described above. In some embodiments, such a content extracting module can be included within the classifier module 130, similar to the define module and the categorize module of the classifier module 130. In other embodiments, such a content extracting module can be operatively coupled to the classifier module 130.

In some embodiments, the classification system 100 can be configured to search, identify and/or classify content that may be relevant or of interest to one or more users of the classification system 100. In such embodiments, the classification system 100 can be configured to receive information associated with the users. In some embodiments, the classification system 100 can be configured to receive user information such as, for example, a user profile, user content history, usage pattern information (e.g., information obtained by a web cookie associated with online activity of a user), a keyword provided by a user, a category associated with a user, and/or the like, from one or more user devices (e.g., the user device 150) operatively coupled to the classification system 100. For example, a communication module of the classifier module 130 can be configured to communicate with and receive user information from the user device 150 that is operated by a user. Similarly, the communication module 236 of the classifier module 200 in FIG. 2 can be configured to communicate with and receive user information from user device(s) operatively coupled to the classifier module 200. For another example, an operator of the classification system 100 can manually enter user information into the classification system 100.

In some embodiments, the content gathering module 110 can be configured to gather content from content host devices (e.g., the content host device 160) operatively coupled to the classification system 100 based on the received user information. For example, the content gathering module 110 can be configured to operate a crawl engine to search one or more predetermined websites based on a set of keywords associated with interests of a user. For another example, the content gathering module 110 can be configured to operate the crawl engine to search messages that are associated with a term of interest and that are posted on an online forum by a user(s). Similar to the approach described above, the content gathering module 110 can be configured to store the gathered content into the database 120.

In some embodiments, the classifier module 130 can be configured to classify content stored in the database 120 based on user information (e.g., a request from a user, a keyword or category associated with interests of a user). Specifically, the define module of the classifier module 130 can be configured to define a training set based on the user information. The categorize module of the classifier module 130 can be configured to categorize the content stored in the database 120 using the training set, in the same method described above. As such, the classifier module 130 can determine whether a piece of available content is related to a user of the classification system 100. Furthermore, if a piece of available content is determined to be related to a user, the classifier module of the classification system 100 can be configured to send an indication that the piece of content is related to the user. In some embodiments, such an indication can be sent to other components of the classification system 100 or other modules operatively coupled to the classification system 100, such that a recommendation message for the piece of content can be sent to the user (e.g., via a user device). In some other embodiments, such an indication can be directly sent to the user.

In some embodiments, a recommendation system (not shown in FIG. 1) operatively coupled to the classification system 100 can be configured to recommend the content, which is determined by the classification system 100 as being related to a user (e.g., related to a term of interest to the user), to that user. Such a content recommendation message can be generated based on, for example, a profile, meta-tags, keywords, categories, and/or usage information associated with the user. In some embodiments, the content recommendation message provided to a user can be, for example, a recommendation for websites, chat rooms, blogs, articles, videos, applications, profiles, locations, Twitter accounts, Facebook profiles, and/or the like. Additionally, the recommendation system can be configured to provide an indication of relevancy (e.g., the relevancy measure) to the user along with the content recommendation message. Such an indication of relevancy can be used to measure a level of recommendation (e.g., strongly recommended, moderately recommended, weakly recommended, etc.) for the content. In some embodiments, the recommendation system can be similar to the recommendation module or recommendation component of the social health system described in the U.S. Provisional Patent Application Ser. No. 61/524,915, filed Aug. 18, 2011, and entitled "System and Method for Exchanging Healthcare Information," which is incorporated herein by reference in its entirety.

Figure 3:
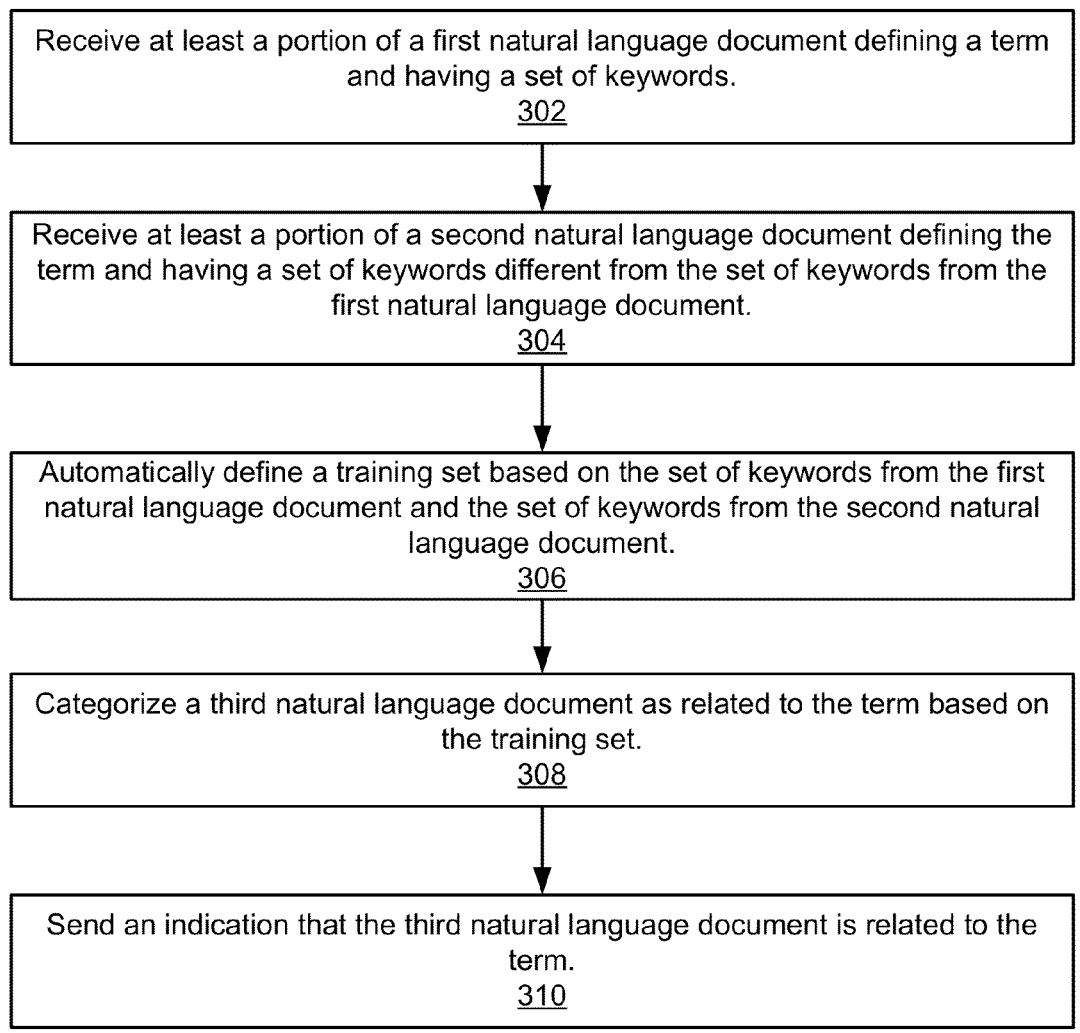
FIG. 3 is a flow chart illustrating a method of classifying content using a training set, according to an embodiment.

FIG. 3 is a flow chart illustrating a method 300 of classifying content using a training set, according to an embodiment. The method 300 can be performed at a classifier module that is structurally and functionally similar to the classifier module 130 in FIG. 1 and the classifier module 200 in FIG. 2. Particularly, instructions associated with performing the method 300 can be stored in a memory of the classifier module (e.g., the memory 220 of the classifier module 200 in FIG. 2) and executed at a processor of the classifier module (e.g., the processor 230 of the classifier module 200 in FIG. 2). Furthermore, similar to the classifier module 130 in FIG. 1, the classifier module performing the method 300 can be included in a classification system (e.g., the classification system 100 in FIG. 1) that is operatively coupled to a content host device (e.g., the content host device 160 in FIG. 1) and/or a user device (e.g., the user device 150 in FIG. 1).

The method 300 includes receiving at least a portion of a first natural language document defining a term and having a set of keywords, at 302. The first natural language document can be, for example, an article, a paper, a message, a post, or any other type of document in a text format. In some embodiments, the portion of the first natural language can be retrieved from the content host device (e.g., a web server) by a content gathering module of the classification system (e.g., the content gathering module 110 of the classification system 100 in FIG. 1) and stored in a database of the classification system (e.g., the database 120 of the classification system 100 in FIG. 1). The term can be a term of interest to a user, or a term associated with a category in the database. The keywords included in the portion of the first natural language document can be associated with defining the term. In some embodiments, the classifier module can be configured to retrieve or receive the portion of the first natural language from the database of the classification system.

Similar to receiving the portion of the first natural language document, the classifier module can be configured to receive at least a portion of a second natural language document defining the term and having a set of keywords, at 304. The second natural language document can be different from the first natural language document. The set of keywords from the second natural language document can be different from the set of keywords from the first natural language document. In some embodiments, the second natural language document can be retrieved from a different content host device (e.g., a different web server) than the content host device hosting the first natural language document.

In some embodiments, the term can be, for example, a medical condition. The first natural language document can be associated with (e.g., published on), for example, a first medical website. In such embodiments, the term can be defined within the first natural language document on the first medical website using the set of keywords from the first natural language document. Furthermore, the portion of the first natural language document can be received from, for example, a crawl engine as a result of the crawl engine searching the first medical website. Such a crawl engine can be operated by the content gathering module of the classification system. Similarly, the second natural language document can be associated with (e.g., published on), for example, a second medical website that is different from the first medical website. The term can be defined within the second natural language document on the second medical website using the set of keywords from the second natural language document. The portion of the second natural language document can be received from the crawl engine as a result of the crawl engine searching the second medical website.

Based on the set of keywords from the first natural language document and the set of keywords from the second natural language document, the classifier module can be configured to automatically define a training set for the term, at 306. In some embodiments, a define module of the classifier module (e.g., the define module 232 of the classifier module 200 in FIG. 2) can be configured to define the training set by identifying a subset of keywords included in the set of keywords from the first natural language document and included in the set of keywords from the second natural language document. In such embodiments, the define module of the classifier module can be configured to define the training set such that the defined training set includes the subset of keywords. In other embodiments, the training set can be defined using any other suitable methods. For example, the training set can be defined as a union of the two sets of keywords, as an intersection of the two sets of keywords, and/or the like.

The classifier module can be configured to categorize a third natural language document as related to the term based on the training set, at 308. In some embodiments, a categorize module of the classifier module (e.g., the categorize module 234 of the classifier module 200 in FIG. 2) can be configured to determine a categorization result for the third natural language document based on the training set. In some embodiments, as described above with respect to FIG. 1, the categorize module of the classifier module can be configured to categorize the third natural language document as related to the term when usage of keywords from the subset of keywords within the third natural language document exceeds a threshold. For example, the third natural language document can be categorized as related to the term if at least a certain number of keywords from the subset of keywords are included in the third natural language document. For another example, the third natural language document can be categorized as related to the term if each of certain keywords from the subset of keywords occurs at least a certain number of times in the third natural language document.

Furthermore, the classifier module can be configured to send an indication that the third natural language document is related to the term, at 310. In some embodiments, a communication module of the classifier module (e.g., the communication module 236 of the classifier module 200 in FIG. 2) can be configured to send the indication to other components of the classification system or other modules operatively coupled to the classification system, such that appropriate actions can be performed accordingly. For example, the indication can be sent to the database of the classification system such that the third natural language document can be associated with an appropriate category and marked as "classified" in the database. For another example, the indication can be sent to a recommendation system operatively coupled to the classification system such that a recommendation for the third natural language document can be provided to a user that is interested in the term. In some embodiments, the communication module of the classifier module can be configured to send the indication to a user that is interested in the term, such that the user can request the third natural language document from the classification system.

In some embodiments, the classifier module can be configured to receive at least a portion of each message from a set of messages posted by a set of users on a website and associated with the term. Such messages can be, for example, posts posted on a public online forum. In response to receiving the portion of each message, the define module of the classifier module can be configured to identify a keyword absent from the training set based on the set of messages when usage of the keyword within the set of messages exceeds a threshold. For example, a keyword can be identified if that keyword is included in at least a certain percentage (e.g., 80%) of the messages. For another example, a keyword can be identified if that keyword occurs at least a certain number of times (e.g., 3 times) in each of at least a certain percentage (e.g., 50%) of the messages.

As a result and as further discussed with respect to FIG. 4, the define module of the classifier module can be configured to modify the training set to include the keyword, thus to define a modified training set for the term. Furthermore, based on the modified training set for the term, the categorize module of the classifier module can be configured to categorize a fourth natural language document as related to the term, and send an indication that the fourth natural language document is related to the term, in a similar approach as described above.

FIG. 4 is a flow chart illustrating a method 400 of modifying a training set used to classify content, according to an embodiment. Similar to the method 300 shown and described with respect to FIG. 3, the method 400 can be performed at a classifier module that is structurally and functionally similar to the classifier module 130 in FIG. 1 and the classifier module 200 in FIG. 2. Particularly, instructions associated with performing the method 400 can be stored in a memory of the classifier module (e.g., the memory 220 of the classifier module 200 in FIG. 2) and executed at a processor of the classifier module (e.g., the processor 230 of the classifier module 200 in FIG. 2). Furthermore, similar to the classifier module 130 in FIG. 1, the classifier module performing the method 400 can be included in a classification system (e.g., the classification system 100 in FIG. 1) that is operatively coupled to a content host device (e.g., the content host device 160 in FIG. 1) and/or a user device (e.g., the user device 150 in FIG. 1).

The method 400 includes categorizing a first natural language document as related to a term based on a training set, at 402. Such a categorization process can be similar to the categorization process described above with respect to the method 300. Specifically, the training set can be previously defined for the term at a define module of the classifier module (e.g., the define module 232 of the classifier module 200 in FIG. 2). A categorize module of the classifier module (e.g., the categorize module 234 of the classifier module 200 in FIG. 2) can be configured to determine a categorization result for the first natural language document based on the training set. In some embodiments, the first natural language document can be associated with (e.g., published on) a first website.

The classifier module can be configured to send an indication that the first natural language document is related to the term, at 404. In some embodiments, a communication module of the classifier module (e.g., the communication module 236 of the classifier module 200 in FIG. 2) can be configured to send such an indication to other components (e.g., a database) of the classification system, other modules (e.g., a recommendation system) operatively coupled to the classification system, or a user that is interested in the term. As a result, appropriate actions can be performed in response to the indication. For example, the first natural language document can be associated with an appropriate category and marked as "classified" in the database. For another example, a recommendation for the first natural language document can be provided to users that are interested in the term.

The classifier module can be configured to receive at least a portion of each message from a set of messages posted by a set of users on a website and associated with the term, at 406. Such messages can be, for example, posts posted on a public online forum that discuss a product associated with the term, articles published on a medical website that provide a new definition for the term, blogs issued from a personal blog that present scientific progress associated with the term, and/or the like. More generally speaking, in some embodiments, a message received at the classifier module can be a signal containing updated content associated with the term or any other keyword related to the term in response to any user action (e.g., modify a post, upload a document, save a file, etc.) that changes (e.g., adds, updates, uploads) the content. In such embodiments, the classifier module can receive such messages from remote and/or local resources (e.g., website, storage device, server, etc.) where the content is changed.

In response to receiving the portion of each message, the define module of the classifier module can be configured to identify a keyword absent from the training set based on the set of messages when usage of the keyword within the set of messages exceeds a threshold, at 408. The usage of the keyword can be represented using any suitable measurement. For example, a keyword can be identified if that keyword is included in at least a certain percentage (e.g., 80%) of the messages. For another example, a keyword can be identified if that keyword occurs at least a certain number of times (e.g., 3 times) in each of at least a certain percentage (e.g., 50%) of the messages.

The define module of the classifier module can be configured to modify the training set to include the keyword in response to the identifying to define a modified training set, at 410. Furthermore, the categorize module of the classifier module can be configured to categorize a second natural language document as related to the term based on the modified training set, at 412. In some embodiments, the second natural language document can be associated with (e.g., published on) a second website different from the first website.

The communication module of the classifier module can be configured to send an indication that the second natural language document is related to the term, at 414. In some embodiments, such an indication can be sent in response to the classifier module receiving an indication of an interest corresponding to the term from a user. Similar to sending the indication of the first natural language document, in some embodiments, the communication module of the classifier module can be configured to send the indication of the second natural language document to other components (e.g., a database) of the classification system, other modules (e.g., a recommendation system) operatively coupled to the classification system, or directly to the user that is interested in the term. As a result, a recommendation for the second natural language document can be provided to the user that is interested in the term, and/or any other appropriate actions can be performed accordingly.

FIG. 5 is a flow chart illustrating a method 500 of defining training sets that are used to classify content, according to an embodiment. Similar to the method 300 and the method 400 shown and described with respect to FIGS. 3 and 4, the method 500 can be performed at a classifier module that is structurally and functionally similar to the classifier module 130 in FIG. 1 and the classifier module 200 in FIG. 2. Particularly, instructions associated with performing the method 500 can be stored in a memory of the classifier module (e.g., the memory 220 of the classifier module 200 in FIG. 2) and executed at a processor of the classifier module (e.g., the processor 230 of the classifier module 200 in FIG. 2). Furthermore, similar to the classifier module 130 in FIG. 1, the classifier module performing the method 500 can be included in a classification system (e.g., the classification system 100 in FIG. 1) that is operatively coupled to a content host device (e.g., the content host device 160 in FIG. 1) and/or a user device (e.g., the user device 150 in FIG. 1).

The method 500 includes defining a training set for a first term based on a set of keywords from a first natural language document defining the first term and a set of keywords from a second natural language document defining the first term, at 502. Such a defining process can be similar to the defining process described above with respect to the method 300. In some embodiments, a define module of the classifier module (e.g., the define module 232 of the classifier module 200 in FIG. 2) can be configured to define the training set by identifying a subset of keywords included in the set of keywords from the first natural language document and included in the set of keywords from the second natural language document. In such embodiments, the define module of the classifier module can be configured to define the training set such that the defined training set includes the subset of keywords. In other embodiments, the training set can be defined using any other suitable methods. For example, the training set can be defined as a union of the two sets of keywords, as an intersection of the two sets of keywords, and/or the like.

In some embodiments, the set of keywords from the first natural language document and the set of keywords from the second natural language document can be produced by crawling a website having the first natural language document and a website having the second natural language document. In some embodiments, the first term can be, for example, a medical condition. The first natural language document can be associated with, for example, a medical website. The first term can be defined within the first natural language document using the set of keywords from the first natural language document. The second natural language document can be associated with, for example, another medical website different from the medical website associated with the first natural language document. Similar to the case of the first natural language document, the first term can be defined within the second natural language document using the set of keywords from the second natural language document.

Similar to defining the training set for the first term, the define module of the classifier module can be configured to define a training set for a second term based on a set of keywords from a third natural language document defining the second term and a set of keywords from a fourth natural language document defining the second term, at 504. In some embodiments, the set of keywords from the third natural language document and the set of keywords from the fourth natural language document can be produced by crawling a website having the third natural language document and a website having the fourth natural language document.

Furthermore, the define module of the classifier module can be configured to define a training set for a third term based on the training set for the first term and the training set for the second term, at 506. The third term can be associated with the first term and the second term. In some embodiments, for example, the first term, the second term, and the third term can be medical conditions. In some embodiment, the third term can include the first term and the second term. As a result, the training set defined for the third term can include at least a portion of the training set for the first term and at least a portion of the training set for the second term.

The classifier module can be configured to categorize a fifth natural language document as related to the third term based on the training set for the third term, at 508. Specifically, a categorize module of the classifier module (e.g., the categorize module 234 of the classifier module 200 in FIG. 2)

can be configured to determine a categorization result for the fifth natural language document based on the training set for the third term, as described above. Furthermore, the classifier module can be configured to send an indication that the fifth natural language document is related to the third term, at 510. In some embodiments, a communication module of the classifier module (e.g., the communication module 236 of the classifier module 200 in FIG. 2) can be configured to send the indication of the fifth natural language document in response to receiving an indication of an interest corresponding to the third term from a user.

In some embodiments, defining the training set for the first term includes identifying a subset of keywords for the first term included in the set of keywords from the first natural language document and included in the set of keywords from the second natural language document. The resulted subset of keywords for the first term is included in the training set for the first term. Similarly, defining the training set for the second term includes identifying a subset of keywords for the second term included in the set of keywords from the third natural language document and included in the set of keywords from the fourth natural language document. The resulted subset of keywords for the second term is then included in the training set for the second term. In such embodiments, defining the training set for the third term can include selecting a subset of keywords for the third term from the subset of keywords for the first term included in for the training set for the first term and from the subset of keywords for the second term included in the training set for the second term.

While some of the examples described herein relate to medical contexts (e.g., medical conditions, medical documents and medical websites), it should be understood that these medical contexts can relate to and include wide range of contexts such as, for example, medical conditions, medicine, health care, and/or the like. For example, such contexts can include homeopathy (e.g., treatments, procedures, medicines), health (e.g., physical condition, mental conditional), fitness (e.g., activity tracking), diet (e.g., nutrition, weight loss goals), sex & relationship (e.g., dating, marital relationships), etc. Natural language documents associated with (e.g., defining) such medical contexts can be hosted at and retrieved from various resources such as a website, a server, a local storage device, etc.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools. Such computer code can also be referred to as a computer program and some embodiments can be in the form of a computer program.

While various embodiments have been described above, it should be understood that they have been presented by way of example only, and not limitation, and as such, various changes in form and/or detail may be made. Any portion of the apparatus and/or methods described herein may be combined in any suitable combination, unless explicitly expressed otherwise. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed is:

1. A non-transitory processor-readable medium storing code representing instructions to be executed by a processor, the code comprising code to cause the processor to:
    receive at least a portion of a first natural language document having (1) a first definition of a medical term, and (2) a first set of keywords associated with the first definition;
    receive at least a portion of a second natural language document having (1) a second definition of the medical term, and (2) a second set of keywords associated with the second definition, the second set of keywords different from the first set of keywords;
    automatically define a training set for the medical term based on the first set of keywords and the second set of keywords;
    categorize a third natural language document as related to the medical term based on the training set; and
    send an indication that the third natural language document is related to the medical term.

2. The non-transitory processor-readable medium of claim 1, wherein:
    the code to define includes code to identify a subset of keywords included in the first set of keywords and included in the second set of keywords, the training set including the subset of keywords; and
    the code to categorize includes code to categorize the third natural language document as related to the medical term when usage of keywords from the subset of keywords within the third natural language document exceeds a threshold.

3. The non-transitory processor-readable medium of claim 1, further comprising code to cause the processor to:
    receive at least a portion of each message from a plurality of messages posted by a plurality of users on a website and associated with the medical term;
    identify a keyword absent from the training set based on the plurality of messages when usage of the keyword within the plurality of messages exceeds a threshold; and
    modify the training set to include the keyword in response to the identifying.

4. The non-transitory processor-readable medium of claim 1, further comprising code to cause the processor to:

receive at least a portion of each message from a plurality of messages posted by a plurality of users on a website and associated with the medical term;

identify a keyword absent from the training set based on the plurality of messages;

modify the training set to include the keyword in response to the identifying to define a modified training set;

categorize a fourth natural language document as related to the medical term based on the modified training set; and send an indication that the fourth natural language document is related to the medical term.

5. The non-transitory processor-readable medium of claim 1, wherein:

the first natural language document is associated with a medical website; and the second natural language document is associated with a medical website different from the medical website associated with the first natural language document.

6. The non-transitory processor-readable medium of claim 1, wherein:

the portion of the first natural language document is received from a crawl engine that searched a website;

the portion of the second natural language document is received from the crawl engine that searched a website different from the website for the first natural language document.

7. A non-transitory processor-readable medium storing code representing instructions to be executed by a processor, the code comprising code to cause the processor to:

receive at least a portion of a first natural language document defining a term and having a set of keywords;

receive at least a portion of a second natural language document defining the term and having a set of keywords different from the set of keywords from the first natural language document;

automatically define a training set based on the set of keywords from the first natural language document and the set of keywords from the second natural language document;

categorize a third natural language document as related to the term based on the training set;

send an indication that the third natural language document is related to the term;

define a training set for a second term based on a set of keywords from a fourth natural language document defining the second term and a set of keywords from a fifth natural language document defining the second term;

define a training set for a third term based on the training set for the first term and the training set for the second term, the third term including the first term and the second term;

categorize a sixth natural language document as related to the third term based on the training set for the third term; and send an indication that the sixth natural language document is related to the third term.

8. The non-transitory processor-readable medium of claim 1, further comprising code to cause the processor to:

receive an indication of an interest of a user, the interest corresponding to the medical term; and send the indication of the third natural language document in response to the indication of the interest of the user.

9. A non-transitory processor-readable medium storing code representing instructions to be executed by a processor, the code comprising code to cause the processor to:

categorize a first natural language document as related to a medical term based on a training set for the medical term;

send an indication that the first natural language document is related to the medical term;

receive at least a portion of each message from a plurality of messages (1) posted by a plurality of users on a website, and (2) associated with the medical term;

identify a keyword absent from the training set based on the plurality of messages when usage of the keyword within the plurality of messages exceeds a threshold;

modify the training set to include the keyword in response to the identifying to define a modified training set for the medical term;

categorize a second natural language document as related to the medical term based on the modified training set; and send an indication that the second natural language document is related to the medical term.

10. The non-transitory processor-readable medium of claim 9, further comprising code to cause the processor to:

receive at least a portion of a third natural language document having (1) a first definition of the medical term, and (2) a first set of keywords associated with the first definition;

receive at least a portion of a fourth natural language document having (1) a second definition of the medical term, and (2) a second set of keywords associated with the second definition, the first set of keywords different from the second set of keywords;

automatically define the training set for the medical term based on the first set of keywords and the fourth set of keywords.

11. The non-transitory processor-readable medium of claim 9, further comprising code to cause the processor to:

receive at least a portion of a third natural language document having (1) a first definition of the medical term, and (2) a first a set of keywords associated with the first definition, the portion of the third natural language document is received from a crawl engine that searched a website;

receive at least a portion of a fourth natural language document having (1) a second definition of the medical term, and (2) a second set of keywords associated with the second definition, the second set of keywords different from the first set of keywords, the portion of the fourth natural language document is received from the crawl engine that searched a website different from the website for the third natural language document;

automatically define the training set for the medical term based on the first set of keywords and the second set of keywords.

12. The non-transitory processor-readable medium of claim 9, wherein:

the first natural language document is associated with a website different from the website associated with the plurality of messages; and the second natural language document is associated with a website different from the website associated with the first natural language document and different from the website associated with the plurality of messages.

13. The non-transitory processor-readable medium of claim 9, wherein the medical term is a first medical term, the non-transitory processor-readable medium further comprising code to cause the processor to:

define a training set for a second medical term based on (1) a first set of keywords from a third natural language document having a first definition of the second medical term, the first definition of the second medical term associated with the first set of keywords, and (2) a second set of keywords from a fourth natural language document having a second definition of the second medical term, the second definition of the second medical term associated with the second set of keywords;

define a training set for a third medical term based on the modified training set for the first medical term and the training set for the second medical term, the third medical term is associated with the first medical term and the second medical term;

categorize a fifth natural language document as related to the third medical term based on the training set for the third medical term; and send an indication that the fifth natural language document is related to the third medical term.

14. The non-transitory processor-readable medium of claim 9, further comprising code to cause the processor to:
receive an indication of an interest of a user, the interest corresponding to the medical term; and
send the indication of the second natural language document in response to the indication of the interest of the user.

15. A non-transitory processor-readable medium storing code representing instructions to be executed by a processor, the code comprising code to cause the processor to:
define a training set for a first medical term based on (1) a set of keywords from a first natural language document having a first definition of the first medical term, and (2) a set of keywords from a second natural language document having a second definition of the first medical term, the set of keywords from the first natural language document associated with the first definition of the first medical term, the set of keywords from the second natural language document associated with the second definition of the first medical term;

define a training set for a second medical term based on (1) a set of keywords from a third natural language document having a first definition of the second medical term, and (2) a set of keywords from a fourth natural language document having a second definition of the second medical term, the set of keywords from the third natural language document associated with the first definition of the second medical term, the set of keywords from the fourth natural language document associated with the second definition of the second medical term;

define a training set for a third medical term based on the training set for the first medical term and the training set for the second medical term, the third medical term is associated with the first medical term and the second medical term;

categorize a fifth natural language document as related to the third medical term based on the training set for the third medical term; and send an indication that the fifth natural language document is related to the third medical term.

16. The non-transitory processor-readable medium of claim 15, wherein:
the first natural language document is associated with a medical website, the first medical term is defined within the first natural language document using the set of keywords from the first natural language document; and
the second natural language document is associated with a medical website different from the medical website associated with the first natural language document, the first medical term is defined within the second natural language document using the set of keywords from the second natural language document.

17. The non-transitory processor-readable medium of claim 15, wherein:
the third medical term includes the first medical term and the second medical term.

18. The non-transitory processor-readable medium of claim 15, wherein:
the training set for the third medical term includes at least a portion of the training set for the first medical term and at least a portion of the training set for the second medical term.

19. The non-transitory process-readable medium of claim 15, wherein:
the set of keywords from the first natural language document, the set of keywords from the second natural language document, the set of keywords from the third natural language document and the set of keywords from the fourth natural language document each is produced by crawling a website having the first natural language document, a website having the second natural language document, a website having the third natural language document and a website having the fourth natural language document.

20. The non-transitory process-readable medium of claim 15, wherein:
the code to define the training set for the third medical term includes selecting a subset of keywords for the third medical term from a set of keywords included in the training set for the first medical term and from a set of keywords included in the training set for the second medical term.

21. The non-transitory process-readable medium of claim 15, wherein:
the code to define the training set for the first medical term includes code to identify a subset of keywords for the first medical term included in the set of keywords from the first natural language document and included in the set of keywords from the second natural language document, the training set for the first medical term including the subset of keywords for the first medical term;
the code to define the training set for the second medical term includes code to identify a subset of keywords for the second medical term included in the set of keywords from the third natural language document and included in the set of keywords from the fourth natural language document, the training set for the second medical term including the subset of keywords for the second medical term;
the code to define the training set for the third medical term includes selecting a subset of keywords for the third medical term from the subset of keywords for the first medical term included in for the training set for the first medical term and from the subset of keywords for the second medical term included in the training set for the second medical term; and
the code to categorize includes code to categorize the fifth natural language document as related to the third medical term when usage of keywords from the subset of keywords for the third medical term within the fifth natural language document exceeds a threshold.

22. The non-transitory processor-readable medium of claim 15, further comprising code to cause the processor to:
receive an indication of an interest of a user, the interest corresponding to the third medical term; and send the indication of the fifth natural language document in response to the indication of the interest of the user.

\* \* \* \* \*